United States Patent [19]
Kaiser et al.

[11] 3,978,089

[45] Aug. 31, 1976

[54] CARYOPHYLLANE EPOXIDE

[75] Inventors: Roman Kaiser, Dubendorf; Dietmar Lamparsky, Wangen-Dubendorf, both of Switzerland

[73] Assignee: Givaudan Corporation, Clifton, N.J.

[22] Filed: July 12, 1973

[21] Appl. No.: 378,478

[30] Foreign Application Priority Data
July 19, 1972   Switzerland.................. 10843/72
July 19, 1972   Switzerland.................. 10844/72

[52] U.S. Cl.............................. 260/345.1; 252/522; 260/348 C; 260/586 F
[51] Int. Cl.$^2$....................................... C07D 311/00
[58] Field of Search................................ 260/345.1

[56] References Cited
OTHER PUBLICATIONS

Naves et al., Chem. Abstracts, vol. 55, entry 11766e (1961).

Nigam et al., Chem. Abstracts, vol. 62, entry 14731e at f (1965).

*Primary Examiner*—John M. Ford
*Attorney, Agent, or Firm*—Thomas Cifelli, Jr.

[57] ABSTRACT

Novel caryophyllane derivatives, a process for their manufacture and odorant compositions containing the novel compounds are disclosed.

1 Claim, No Drawings

CARYOPHYLLANE EPOXIDE

FIELD OF THE INVENTION

This invention relates to the field of odorants.

SUMMARY OF THE INVENTION

The present invention relates to caryophyllane derivatives. More particularly, the invention is concerned with caryophyllane derivatives and a process for the manufacture thereof. The invention is also concerned with odorant compositions containing said caryophyllane derivatives and with a method of imparting an odour to products by means of said derivatives.

The caryophyllane derivatives with which the present invention is concerned have the following general formula

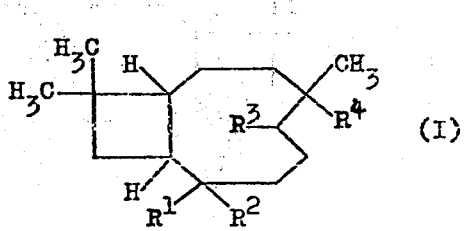

wherein $R^1$ and $R^2$ together represent an oxo group and $R^3$ and $R^4$ together represent a C—C bond or $R^1$ represents a methyl group, $R^2$ and $R^4$ together represent an epoxide group and $R^3$ represents a hydrogen atom.

It will be appreciated that formula I hereinbefore embraces 12-norcaryophyll-6-en-3-one of the formula

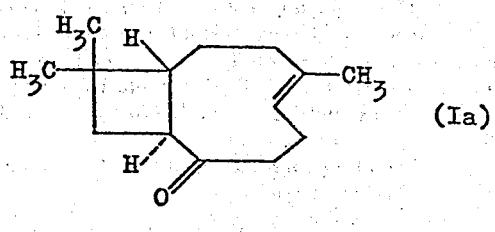

and 3,7-caryophyllane epoxide of the formula

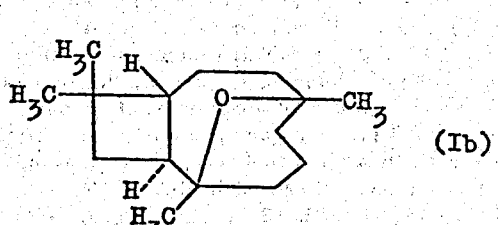

Thus, this invention is concerned, in one of its aspects, with the novel 12-norcaryophyll-6-en-3-one and the hitherto unknown 3,7-caryophyllane epoxide insofar as it is synthetically manufactured as well as with 3,7-caryophyllane epoxide in substantially pure form or in admixture with other odorants and/or solvents or carriers, with the exception of verbena oil.

DESCRIPTION OF THE PREFERRED EMBODIMENTS

The fundamental substance from which the compounds of formula I are derived is caryophyllene of the formula

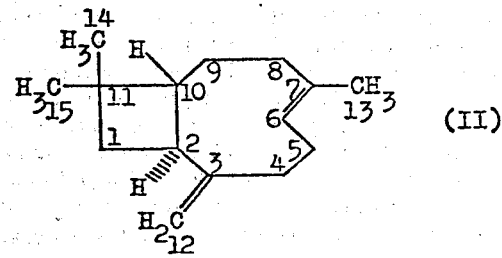

Caryophyllene occurs widely in nature in essential oils, primarily in clove oil (Eugenia caryophyllata) from which it can be isolated in admixture with about 10% humulene. Pure caryophyllene can readily be produced from commercial caryophyllene by column chromatography on Kieselgel.

The hitherto unknown 3,7-caryophyllane epoxide of formula Ib has been found in small amounts in verbena oil from which it can be isolated in accordance with known methods, preferably by distillation and chromatography.

Natural verbena oil is obtained by steam distillation from Lippia citriodora Kunth. (= Verbena triphylla l'Herit = Aloysia citriodora Ort.) which is indigenous to South America and which is principally cultivated there. Natural verbena oil is very valuable in the perfume industry because of its fine lemon-like odour with a balsamic foundation. It is, however, very expensive and relatively difficult to obtain commercially, this being related to the special climatic conditions which are a prerequisite for the cultivation of the plants. On the other hand, verbena oil with a favourable price structure can be widely used in all fields of the perfume industry, especially in eaux de Cologne.

3,7-Caryophyllane epoxide of formula Ib itself has a woody, balsamic odour. As has been found, the addition of 3,7-caryophyllane epoxide to many odorant compositions imparts thereto more depth and tenacity. Also, it has a strong modifying action in combination with individual odorants (e.g. citral). This epoxide can accordingly be used, with advantage, for imparting a bouquet to citral and citral-like odorants such as occur, amongst others, in verbena oil. It can, moreover, be quite generally used as an odorant for the manufacture of odorant compositions such as perfumes or for perfuming technical or cosmetic products of all kinds such as, for example, solid or liquid detergents, synthetic washing agents, aerosols, soaps, lotions, creams etc.

The content of 3,7-caryophyllane epoxide in odorant compositions or in perfumed products can vary within wide limits. In perfume compositions it can be present in an amount of between about 0.01 and 20 wt %, preferably between 2 and 10 wt %, and in finished products such as soaps, lotions, creams it can preferably be present in an amount of between 0.01 and 0.5 wt %.

12-Norcaryophyll-6-en-3-one of formula Ia likewise possesses particular fragrance qualities. It possesses a woody, somewhat earthy fragrance partially reminiscent of sandal or vetiver. The addition of 12-norcaryophyll-6-en-3-one to odorant compositions imparts thereto a warmer and fuller odour. 12-Norcaryophyll-6-en-3-one blends especially well with woody smelling compositions and essential oils. It can accordingly be used as an odorant in the perfume industry; for example for the manufacture of, or for modifying the odour of, odorant compositions such as perfumes, perfume bases etc, by the addition of olfactory perceptible amounts (e.g. 0.1 -10 wt %) to mixtures of known odorants. One of a wide field of application is, for example, the manufacture of chypre type odorant compositions. 12-Norcaryophyll-6-en-3-one can also be used for the perfuming of technical and cosmetic products of all kinds; for example solid and liquid detergents, synthetic washing agents, aerosols, soaps, creams, lotions etc in concentrations of, for example, about 0.02-0.1 wt %.

According to the process provided by the present invention, the caryophyllane derivatives of formula I hereinbefore are manufactured by a. reductively eliminating the 6,7-epoxy group of a 6,7-epoxy-12-norcaryophyllan-3-one of the formula

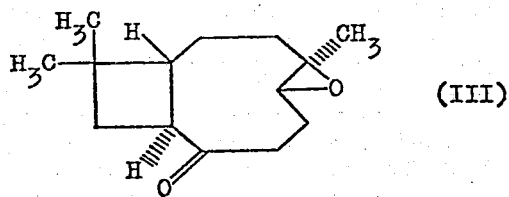

(III)

to give 12-norcaryophyll-6-en-3-one of formula Ia hereinbefore, or b. cyclizing caryophyll-6-en-3-ol of the formula

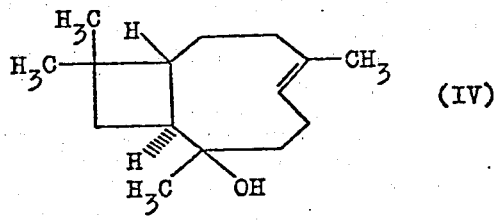

(IV)

with the formation of a 3,7-epoxy group to give 3,7-caryophyllane epoxide of formula Ib hereinbefore.

The reductive elimination of the 6,7-epoxy group of 6,7-epoxy-12-norcaryophyllan-3-one of formula III according to embodiment (a) of the process can be carried out in a manner known per se; for example, by treatment with a chromium (II)-ethylenediamine complex [I. K. Kochi et al., Tetrahedron 24, 3503 (1968)] or by means of weakly coppered zinc in boiling ethanol [S. M. Kupchan and M. Marnyama, J. Org. Chem. 36, 1187 (1971)].

The cyclization of caryophyll-6-en-3-ol according to embodiment (b) of the process can also be carried out in a manner known per se by treatment with an acid catalyst such as an inorganic acid, a Lewis acid or an organic sulphonic acid (e.g. p-toluenesulphonic acid, boron trifluoride etherate or a 1:1 mixture of boron trifluoride and phosphoric acid) in one of the usual inert organic solvents such as dioxane, diethyl ether, benzene, toluene etc. The treatment can be carried out within a wide temperature range, preferably at between 0°C and the reflux temperature of the mixture.

The working up of the mixture and the isolation and purification of the 3,7-caryophyllane epoxide can be carried out according to known methods. Chromatography on Kieselgel is an especially suitable purification method.

The preparation of 6,7-epoxy-12-norcaryophyllan-3-one of formula III from caryophyllene of formula II can be carried out in a manner known per se via 6,7-epoxycaryophyllene of the formula

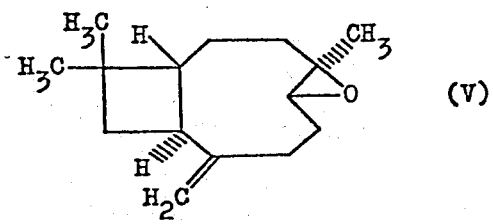

(V)

The conversion of 6,7-epoxycaryophyllene of formula V into 6,7-epoxy-12-norcaryophyllan-3-one of formula III can be carried out, for example, by ozonolysis of the exocyclic double-bond or by oxidation with permanganate, while the selective epoxidation of the endocyclic double-bond of caryophyllene can be carried out by means of a peracid (e.g. peracetic acid) in a suitable solvent (e.g. methylene chloride) and in the presence of sodium acetate.

12-Norcaryophyll-6-en-3-one of formula Ia can be converted by reaction with a GRIGNARD compound of the formula $H_3C$—Mg—Hal (in which Hal stands for a chlorine, bromine or iodine atom) in a known manner into caryophyll-6-en-3-ol of formula IV which is used as the starting material for embodiment (b) of the process.

The following Examples illustrate the process provided by the invention:

EXAMPLE 1

A mixture of 2.22 g of 6,7-epoxy-12-norcaryophyllan-3-one [(Kobuson), see Chem. Pharm. Bull. 17, 1390 (1969)], 88 g of weakly coppered zinc [R. D. Smith and H. B. Simmens, Org. Syn. 41, 72 (1961)] and 400 ml of ethanol is heated under reflux for 35 hours. After cooling the mixture, the precipitate is filtered off and the filtrate concentrated under reduced pressure. Chromatography of the crude product on Kieselgel yields 1.7 g of pure 12-norcaryophyll-6-en-3-one. IR: $\nu_{max}=$ 2930, 2858, 1695, 1450, 1381, 1369, 1351, 1331, 1279, 1225, 1160, 1113, 1090, 1059, 1018, 990 and 811 cm$^{-1}$. The compound has a woody, slightly camphoraceous odour reminiscent of sandal, vetiver and cedar.

EXAMPLE 2

A solution of 1.11 g of caryophyll-6-en-3-ol and 0.1 g of p-toluenesulphonic acid in 20 ml of benzene is stirred for 30 minutes at a temperature of 5°C. The mixture is then diluted with twice the amount of benzene, washed with soda solution and water, dried and concentrated under reduced pressure. Chromatography of the resulting crude product on Kieselgel yields 0.35 g (31.5%) of 3,7-caryophyllane epoxide and 0.6 g of hydrocarbon compounds. The epoxide has a woody, balsamic odour. IR: $\nu_{max}$ = 2930, 2860, 1460, 1370, 1281, 1231, 1210, 1180, 1117, 1099, 1075, 1058, 989, 969, 900, 840 and 815 cm$^{-1}$.

EXAMPLE 3

A mixture of 1.11 g of caryophyll-6-en-3-ol, 0.2 g of boron trifluoride ethyl etherate and 20 ml of ether is heated under reflux for 50 minutes. The mixture is then mixed with twice the amount of ether, washed with soda solution and water, dried and concentrated under reduced pressure. Chromatography of the resulting crude product on Kieselgel yields 0.1 g (9%) of 3,7-caryophyllane epoxide and 0.7 g of hydrocarbon compounds.

The starting material can be prepared as follows:

To a Grignard reagent prepared from 0.48 g of magnesium and 2.8 g of methyl iodide is added dropwise in the course of 5 minutes a solution of 3 g of 12-norcaryophyll-6-en-3-one in 15 ml of ether. After 15 minutes, the mixture is carefully treated, with ice cooling, with a concentrated ammonium chloride solution and then extracted with ether. The ethereal phase is washed with water, dried over sodium sulphate and concentrated. Bulb-tube distillation of the residue yields 3.05 g (94% of theory) of pure caryophyll-6-en-3-ol. IR: $\nu_{max}$ = 3490, 2920, 2856, 1670, 1450, 1380, 1366, 1280, 1274, 1199, 1105, 1080, 1052, 990, 939, 890, 871, 855, 820 and 800 cm$^{-1}$. The compound has a woody, earthy, patchouli-type odour.

The following Examples illustrate typical odorant compositions provided by this invention:

EXAMPLE A

Odorant composition containing 12-norcaryophyllan-6-en-3-one

|  | Parts by weight |
|---|---|
| γ-Methylionone | 100 |
| Lavandin 22/24 | 100 |
| α-Isomethylionone | 80 |
| Amyl salicylate | 50 |
| Eugenol | 50 |
| Linalyl acetate | 50 |
| Galbanum oil 10%* | 40 |
| Iris resinoid | 40 |
| Methylnonylacetaldehyde 10%* | 40 |
| 2-Heptylcyclopentanone 10%* | 40 |
| Petitgrain oil Paraguay | 40 |
| Vetiveryl acetate | 40 |
| Sauge sclaree | 20 |
| Orange oil Ital. | 30 |
| Bergamotte oil Reggio | 30 |
| Lemon oil Ital. | 10 |
| Terpineol | 30 |
| Geranium oil Bourbon | 20 |
| Musk ketone | 20 |
| Vetiver oil Bourbon | 15 |
| Ylang-Ylang oil | 15 |
| 12-Norcaryophyll-6-en-3-one | 50 |
| Sandalwood oil | 30 |
| Heliotropin | 30 |
| Coumarin | 30 |
|  | 1000 |

*in phthalic acid diethyl ester

The composition has a pronounced woody-spicy character and is suitable for the perfuming of male cosmetics.

EXAMPLE B

Odorant composition containing 3,7-caryophyllane epoxide

|  | Parts by weight |
|---|---|
| Cinnamon aldehyde | 100 |
| Lavender oil | 100 |
| Geranium oil Bourbon | 100 |
| Sandela Givaudan | 100 |
| Baccartol Givaudan | 60 |
| Terpineol | 80 |
| para-Tertiary butyl-cyclohexyl acetate | 50 |
| Amylsalicylate | 50 |
| Phenylethyl alcohol | 50 |
| α-Methylionone | 50 |
| Coumarin | 30 |
| Musk ambrette | 30 |
| Resinoid storax | 50 |
| Petitgrain oil Paraguay | 50 |
| Patchouli oil | 20 |
| 1,1,4,4-Tetramethyl-6-ethyl-7-acetyl-1,2,3,4-tetrahydronaphthalene | 30 |
| 3,7-Carophyllane epoxide | 50 |
|  | 1000 |

The foregoing composition has a fantasy-floral note which is especially suitable for the perfuming of soap.

By the addition of 3,7-caryophyllane epoxide, the composition is given more tenacity and depth. The base acts somewhat woody and warmer.

What we claim is:

1. Substantially pure 3,7-caryophyllane epoxide.

* * * * *